United States Patent [19]
Stouder, Jr.

[11] Patent Number: 5,882,344
[45] Date of Patent: *Mar. 16, 1999

[54] ADJUSTABLE LENGTH CANNULA AND TROCAR

[76] Inventor: Albert E. Stouder, Jr., 318 N. West St., Tipton, Ind. 46072

[*] Notice: This patent issued on a continued prosecution application filed under 37 CFR 1.53(d), and is subject to the twenty year patent term provisions of 35 U.S.C. 154(a)(2).

[21] Appl. No.: 544,722

[22] Filed: Oct. 18, 1995

[51] Int. Cl.⁶ .................. A61M 5/00; A61M 25/00
[52] U.S. Cl. .................. 604/264; 604/117; 604/158; 604/164; 604/905
[58] Field of Search .................. 604/117, 158, 604/169, 165, 179, 175, 198, 240, 241, 269, 283, 905

[56] References Cited

U.S. PATENT DOCUMENTS

| | | | |
|---|---|---|---|
| 219,866 | 4/1879 | Gruskin | 128/315 |
| 1,538,678 | 5/1925 | Blinn . | |
| 2,338,800 | 1/1944 | Burke | 128/215 |
| 2,457,464 | 12/1948 | Grose | 128/347 |
| 2,705,949 | 4/1955 | Silverman | 128/2 |
| 3,077,194 | 2/1963 | Walden et al. | 128/343 |
| 3,575,160 | 4/1971 | Vass et al. | 128/2 R |
| 3,750,667 | 8/1973 | Pshenichny et al. | 128/215 |
| 3,783,876 | 1/1974 | Dye | 128/347 |
| 4,112,932 | 9/1978 | Chiulli | 128/3 |
| 4,270,537 | 6/1981 | Romaine | 128/218 |
| 4,710,171 | 12/1987 | Rosenberg | 604/117 |
| 4,940,458 | 7/1990 | Cohn | 604/51 |
| 5,066,288 | 11/1991 | Deniega et al. | 604/274 |
| 5,092,376 | 3/1992 | Blankenship et al. | 141/25 |
| 5,147,376 | 9/1992 | Pianetti | 606/170 |
| 5,183,465 | 2/1993 | Xanthakos et al. | 604/108 |
| 5,190,521 | 3/1993 | Hubbard et al. | 604/51 |
| 5,201,714 | 4/1993 | Gentelia et al. | 604/167 |
| 5,250,026 | 10/1993 | Ehrlich et al. | 604/60 |
| 5,273,545 | 12/1993 | Hunt et al. | 604/167 |
| 5,279,567 | 1/1994 | Ciaglia et al. | 604/117 |
| 5,368,046 | 11/1994 | Scarfone et al. | 128/754 |
| 5,380,292 | 1/1995 | Wilson | 604/164 |
| 5,505,710 | 4/1996 | Dorsey, II | 604/164 |

OTHER PUBLICATIONS

Iotec Industries brochure: "IOTEC Trocars Line Up for Sharp Savings", 1995.

*Primary Examiner*—Wynn Wood Coggins
*Assistant Examiner*—Jennifer R. Sadula
*Attorney, Agent, or Firm*—Woodard, Emhardt, Naughton Moriarty & McNett

[57] ABSTRACT

An adjustable length cannula which may be longitudinally extended or retracted in order to accommodate a range of body cavity wall thicknesses. The cannula includes an annular flange which abuts the skin surface to provide lateral stability to the inserted cannula and to prevent the associated trocar from being inserted too far into the body cavity. A low external profile of the cannula further contributes to its lateral stability. An adjustable length trocar for use with one embodiment of the adjustable length cannula is also disclosed.

24 Claims, 7 Drawing Sheets

Fig. 21

ADJUSTABLE LENGTH CANNULA AND TROCAR

TECHNICAL FIELD OF THE INVENTION

The present invention generally relates to cannulas and trocars used to puncture tissue for the performance of laparoscopic or arthroscopic surgery and, more particularly, to an adjustable length cannula and trocar.

BACKGROUND OF THE INVENTION

Prior to laparoscopic or arthroscopic surgery, a cannula is inserted through the skin to access a body cavity through the cannula tube. In order to penetrate the skin, the distal end of the cannula tube is placed against the skin and a trocar is inserted through the tube. By pressing against the proximal end of the trocar, the point of the trocar is forced through the skin until it enters the body cavity. At this time, the cannula tube in inserted through the perforation made by the trocar and the trocar is withdrawn, leaving the cannula tube as an access way into the body cavity.

It has been found that often a great deal of force is required to cause the trocar point to penetrate the skin and underlying tissue. When the point finally breaks through this tissue, resistance to penetration is suddenly removed, and the trocar point can suddenly penetrate to reach internal organs of the body, which may cause lacerations and other injury to the internal organs.

For this reason, when a laparoscopy is performed, a pneumoperitoneum is first performed by introducing into the peritoneal cavity 3–4 liters of $CO_2$. The pneumoperitoneum causes rising of the front abdominal wall and separation of the internal organs thereof and in particular, if the patient is placed into a slight Trendelemburg's position, the internal organs tend to move to the upper abdominal region. The trocar needle must then be introduced at an angle of 45° in the lower periumbilical seat after sectioning of the skin (in a semi-circle around the lower edge of the navel) and the subcutis until reaching the aponeurosis. In addition, the trocar must be pushed carefully to avoid sudden deep penetration which could injure the internal organs or large vessels. However, despite all of these precautions, it is not always possible to avoid traumatic complications of the anatomic structures mentioned above and the complications connected with the pneumoperitoneum.

An additional problem in current laparoscopic procedures is that the thickness of abdominal tissue which must be traversed by the cannula tube varies from patient to patient. Because of this, a variety of different length cannulas are available for use in laparoscopic procedures, requiring the doctor to estimate the thickness of the abdominal tissue for the particular patient and then select a cannula having the proper length. Additionally, the present fixed length cannulas also contain no means for stabilizing the cannula against the surface of the patient's body. The result is that movement of the cannula during the laparoscopic procedure can cause tissue trauma in the area of skin surrounding the cannula. The surgeon performing the laparoscopic procedure must therefore stabilize the top of the cannula tube with one hand while using the other hand to insert the laparoscopic instrument into the cannula tube. Finally, present cannula tubes protrude from the skin's surface a substantial distance, which contributes to their general instability, easily becoming entangled in tubes and other devices used in the surgical procedure.

There is therefore a need in the prior art for a cannula tube which may be used to penetrate varying thicknesses of abdominal tissue, which provides a stable interface between the cannula and the patient and which exhibits a low profile above the surface of the patient's skin. Additionally, there is a need in the prior art for a trocar which will minimize the chance of accidental trauma to the abdominal organs due to penetration of the trocar to too great a depth within the abdominal cavity. The present invention is directed toward meeting these needs.

SUMMARY OF THE INVENTION

The present invention relates to an adjustable length cannula which may be longitudinally extended or retracted in order to accommodate a range of body cavity wall thicknesses. The cannula includes an annular flange which abuts the skin surface to provide lateral stability to the inserted cannula and to prevent the associated trocar from being inserted too far into the body cavity. A low external profile of the cannula further contributes to its lateral stability. An adjustable length trocar for use with one embodiment of the adjustable length cannula is also disclosed.

In one form of the invention, an adjustable length cannula for insertion through a body cavity wall is disclosed comprising a body member having a first exterior surface; a first interior surface defining a first longitudinal passageway; a first thread on the first interior surface; and a cannula member having a second exterior surface; a second interior surface defining a second longitudinal passageway; a second thread on the second exterior surface, the first and second threads being interengaged in order to allow the cannula member to telescope within the first longitudinal passageway; wherein at least a porton of the first and second threads lie below a skin surface when the adjustable length cannula is inserted through the body cavity wall.

In another form of the invention, an adjustable length cannula for insertion through a body cavity wall is disclosed, comprising a body member having a first exterior surface; a first interior surface defining a first longitudinal passageway; a first incremental spacing member on the first interior surface; and a first thread on the first exterior surface; a cannula member having a second exterior surface; a second interior surface defining a second longitudinal passageway; and a second incremental spacing member on the second exterior surface, the first and second incremental spacing members being interengaged in order to allow the cannula member to telescope within the first longitudinal passageway; and a collet clamp having a third exterior surface; a third interior surface defining a third longitudinal passageway; a second thread on the third interior surface, the first and second threads being interengaged in order to allow the body member to telescope within the third longitudinal passageway; and an annular flange on the third exterior surface; wherein the annular flange abuts a skin surface when the adjustable length cannula is inserted through the body cavity wall.

In another form of the invention, an adjustable length trocar is disclosed, comprising a longitudinal shaft; a handle at a proximal end of the shaft; a pointed tip at a distal end of the shaft; an upper trocar housing rotatably coupled to the longitudinal shaft and having a first exterior surface; a first interior surface; a first thread on the first interior surface; and a lower trocar housing having a second exterior surface; a second interior surface defining a longitudinal passageway; and a second thread on the second exterior surface, the first and second threads being interengaged in order to allow the longitudinal shaft to telescope within the longitudinal passageway.

DETAILED DESCRIPTION OF THE PREFERRED EMBODIMENTS

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 6:
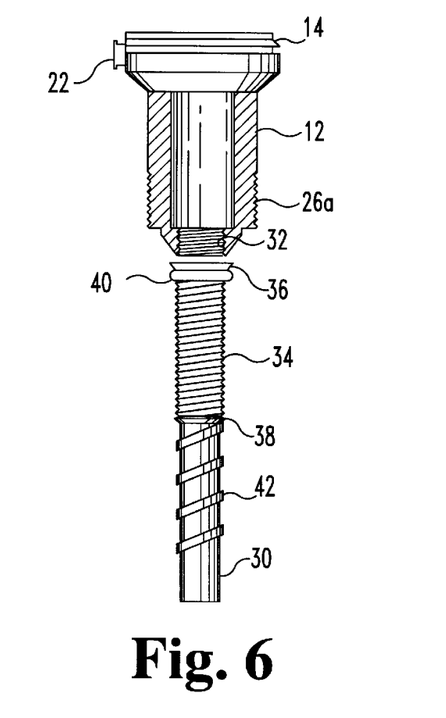
FIG. 6 is a partial cross-sectional side view of the body member and cannula member of the first embodiment adjustable length cannula of the present invention.

The present invention involves the use of a single cannula which may be adjusted to any desired length within a fixed range. Such adjustability allows the cannula to be used with a variety of body cavity wall thicknesses. A first embodiment of such an adjustable length cannula is illustrated in partial cross-sectional side view in FIG. 1 and is indicated generally at 10. Adjustable length cannula 10 comprises a body member 12 which is generally cylindrical in shape and illustrated in a partial cross-sectional view in FIGS. 1, 2 and 6. The body member 12 preferably includes either ridges or threads 14 near a top surface thereof in order to facilitate connection of a cap 16. Lying between the body member 12 and the cap 16 is a suitable main seal 18, such as a silicone slit seal, which helps to provide an airtight seal around instruments which are passed through the central channel of the adjustable length cannula 10. Furthermore, the cap 16 includes a slide 20 disposed therethrough, the slide 20 containing a plurality of secondary seals of various sizes in order to accommodate instruments of varying diameter which may be passed through the adjustable length cannula 10. The slide 20 is preferably constructed in accordance with the teachings of U.S. Pat. No. 5,350,362, issued to the same inventor as the present application. The body member 12 optionally includes a side port 22 which communicates between the exterior and interior of the body member 12, as is known in the art. If the optional side port 22 is present, then the cap 16 preferably includes a notch 24 in order to provide clearance for the side port 22.

Figure 1:
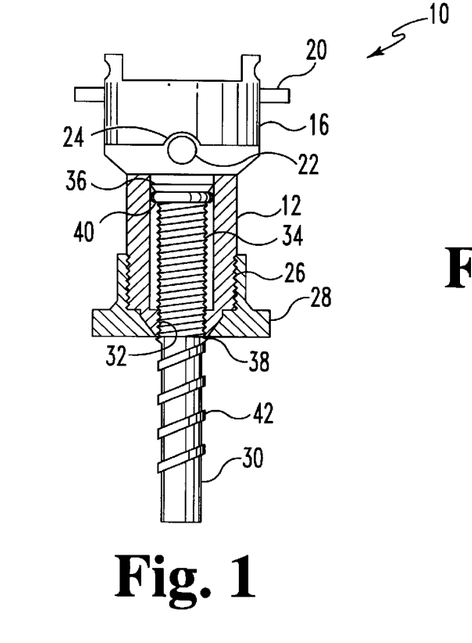
FIG. 1 is a partial cross-sectional side view of a first embodiment adjustable length cannula of the present invention.
Figure 2:
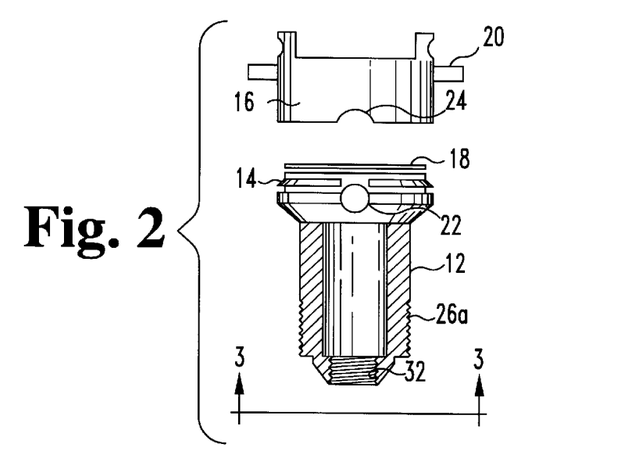
FIG. 2 is a partial cross-sectional side view of a cap and body member of the first embodiment adjustable length cannula of the present invention.
Figure 3:
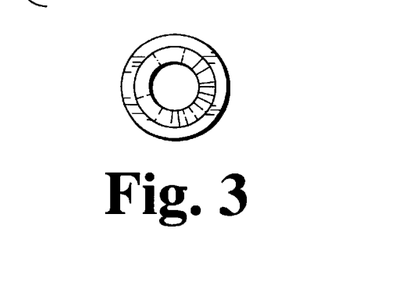
FIG. 3 is a bottom plan view of the body member of the first embodiment adjustable length cannula of the present invention.
Figure 4:
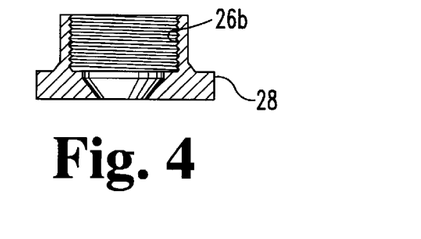
FIG. 4 is a cross-sectional view of a collet clamp of the first embodiment adjustable length cannula of the present invention.
Figure 5:
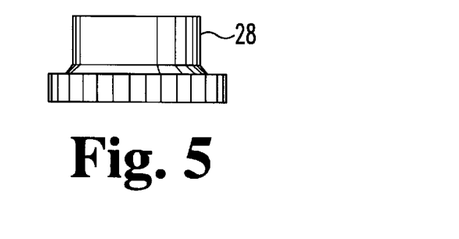
FIG. 5 is a side elevational view of the collet clamp of the first embodiment adjustable length cannula of the present invention.

Attached to the exterior of the body member 12 by means of threads 26 is a collet clamp 28. As will be explained in greater detail hereinbelow, the collet clamp 28 provides a stable platform for the adjustable length cannula in order to minimize trauma to the surrounding tissue.

The adjustable length cannula 10 further includes a sliding cannula member 30 which is adjustably engaged with the body member 12 by means of interaction between incremental spacing members 32 on the body member 12 and incremental spacing members 34 on the cannula member 30. In order to provide adjustability of the longitudinal position of the cannula member 30 within the body member 12, the incremental spacing members 32 and 34 may comprise complementary threaded surfaces. Alternatively, the incremental spacing members 32 may comprise one or more raised ribs while the incremental spacing members 34 may comprise a plurality of indentations, or vise versa. It will therefore be appreciated by those skilled in the art that interaction between the incremental spacing members 32 and 34 allow the cannula member 30 to be extracted from or inserted into the body member 12 over a limited range in order to adjust the longitudinal length of the adjustable length cannula 10. The raised lips 36 and 38 on the cannula member 30 limit the longitudinal travel of the cannula member 30 into and out of the body 12. The cannula member 30 carries an O-ring seal 40 in order to prevent passage of gases or liquids around the exterior of the cannula member 30. The cannula member 30 further includes an external thread 42 around the distal section thereof, in order to facilitate insertion of the adjustable length cannula 10 and retention thereof within the body cavity during the laparoscopic procedure. In operation, the relative positioning of incremental spacing members 32 and 34 is adjusted in order to lengthen or shorten the adjustable length cannula 10 to a longitudinal dimension appropriate for the patient. A trocar (not shown) is then inserted through the slide seal 20, the main seal 18 and through the central channel of the cannula member 30 until the pointed distal tip of the trocar protrudes from the distal end of the cannula member 30. The adjustable length cannula 10 is then inserted through the patient's abdominal tissue (for example) with a pushing and twisting motion until the annular flange at the bottom of the collet clamp 28 reaches the surface of the patient's skin. Because the contact of the collet clamp 28 with the patient's skin prevents further insertion of the adjustable length cannula 10, the danger of inserting the trocar/adjustable length cannula 10 too far into the abdominal cavity, thereby potentially injuring intra-abdominal organs, is eliminated.

Furthermore, the action of the screw thread 42 as the adjustable length cannula 10 is inserted through the abdominal tissue tends to compress the abdominal wall in the area of insertion between the thread 42 and the collet clamp 28. The result is that the abdominal tissue is compressed between the outer skin and the fascia in the area of the adjustable length cannula 10, thereby providing greater stability to the adjustable length cannula 10. Furthermore, the broad surface area of the collet clamp 28 provides a stable platform to prevent excessive motion of the adjustable length cannula 10 after insertion. Not only do these features reduce tissue trauma of the abdominal wall due to decreased movement of the adjustable length cannula 10, but they also obviate the need for the surgeon to steady the cannula with one hand while inserting, operating and extracting instruments through its central channel. A further advantage of the adjustable length cannula 10 is that a single cannula may be used for a wide range of abdominal wall thicknesses.

Figure 7:
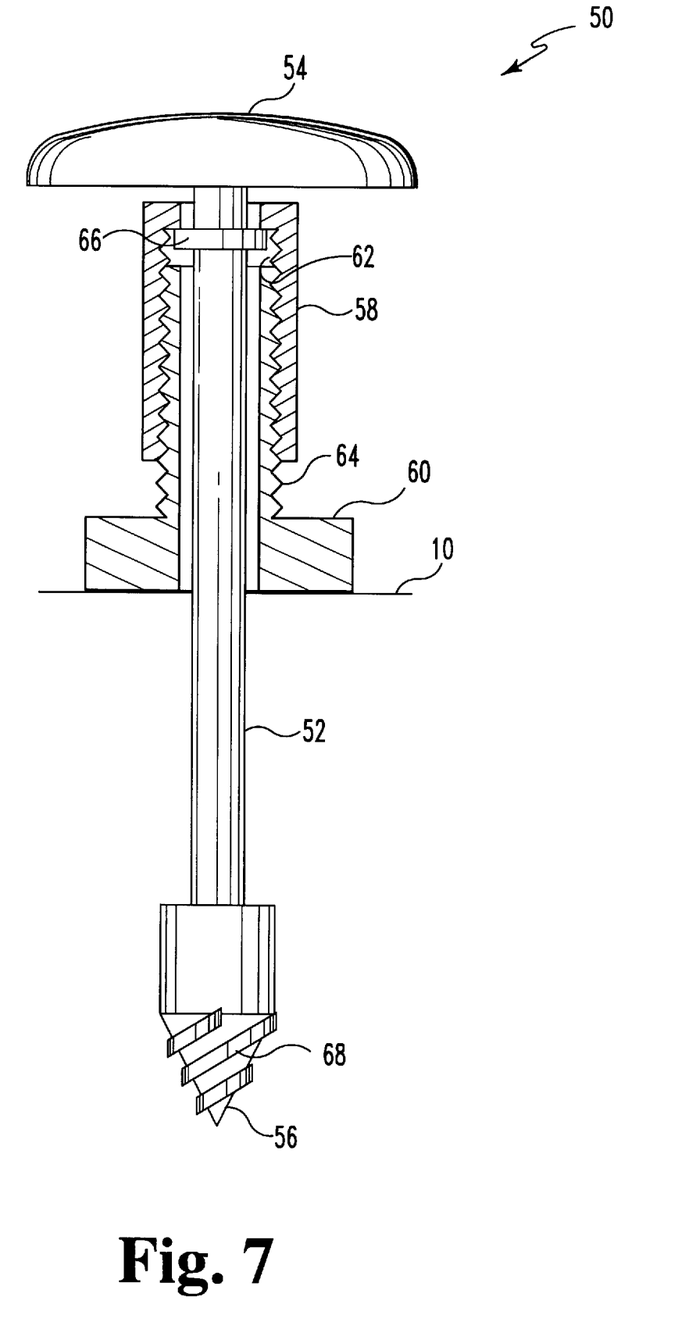
FIG. 7 is a partial cross-sectional side view of a first embodiment adjustable length trocar of the present invention.

Referring now to FIG. 7, there is shown a first embodiment adjustable length trocar of the present invention indicated generally at 50. Because the adjustable length cannula 10 of FIG. 1 may be adjusted to a wide range of longitudinal lengths, it is necessary to provide a trocar for use with the adjustable length cannula which may also be adjusted in longitudinal length. The trocar 50 of FIG. 7 incorporates this feature. The trocar 50 consists of a longitudinal shaft 52 terminated by a disc-shaped handle 54 at its proximal end and a pointed tip 56 at its distal end. The trocar shaft 52 is partially contained within an upper trocar housing 58 and a lower trocar housing 60. The relative longitudinal positions of upper trocar housing 58 and lower trocar housing 60 are adjustable within a limited range by interaction of the threads 62 and 64.

The trocar shaft 52 includes an annular flange 66 fixedly attached thereto. Because the upper surface of the upper trocar housing 58 is held between the annular flange 66 and the trocar handle 54, the longitudinal length of the adjustable length trocar 50 (between the bottom surface of the trocar housing 50 and the distal tip 56) may be adjusted by varying the position of the upper trocar housing 58 with respect to the lower trocar housing 60. The bottom surface of the bottom trocar housing 60 rests on the upper surface of the adjustable length cannula 10, and the threads 62 and 64 are adjusted until the tip 56 of the adjustable length trocar 50 extends through the distal portion of cannula member 30. Once such positioning has been achieved, then the combination adjustable length cannula 10 and adjustable length trocar 50 may be inserted into the patient as described above. The adjustable length trocar 50 may optionally be provided with an auger screw thread 68 on the pointed distal tip 56 in order to facilitate insertion of the adjustable length trocar 50 through the abdominal wall. A very controlled insertion may be achieved by twisting the adjustable length trocar 50 and the adjustable length cannula 10, thereby allowing the screw threads 68 and 42 to draw the device into the abdominal wall. This provides a much more precise insertion than the prior art devices in which the pointed trocar is simply pushed through the abdominal wall.

Figure 8:
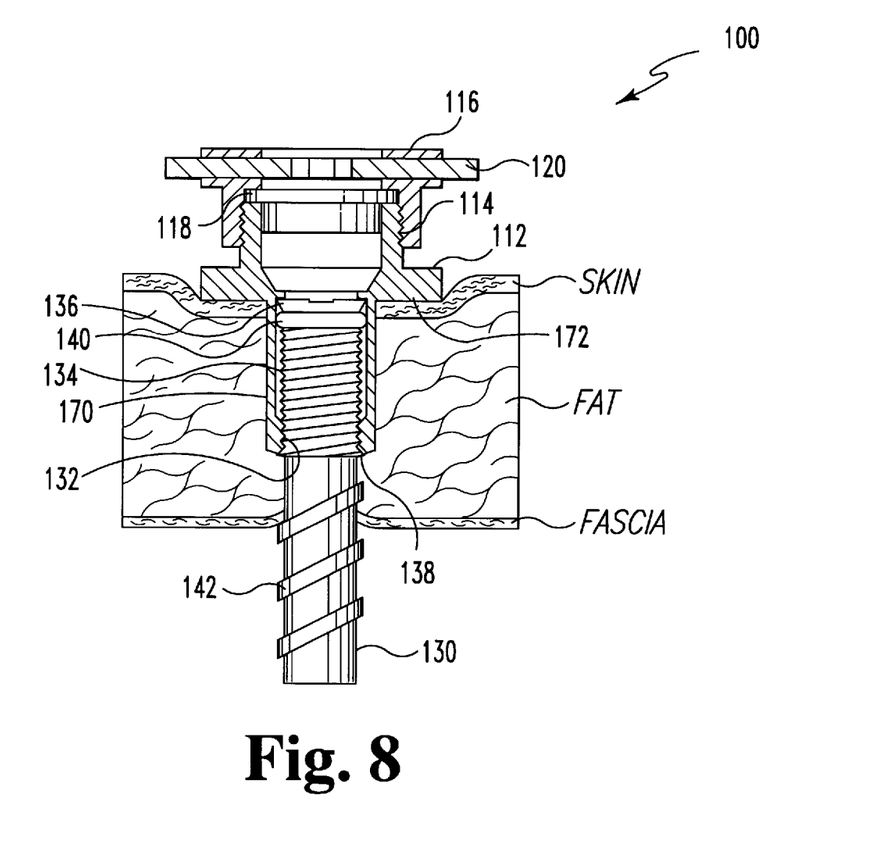
FIG. 8 is a partial cross-sectional side view of a second embodiment adjustable length cannula of the present invention inserted through a wall of a body cavity.
Figure 13:
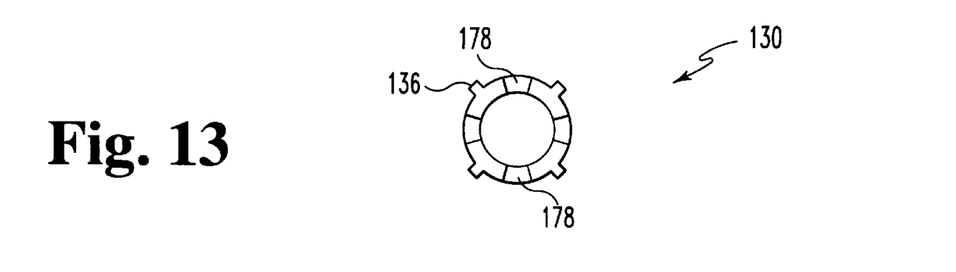
FIG. 13 is a top plan view of the cannula member of FIG. 12.

Referring now to FIG. 8, a second embodiment variable length cannula is illustrated in partial cross-sectional side view, and indicated generally at 100. The adjustable length cannula 100 is shown inserted through a patient's abdominal wall, comprising a skin layer, a fat layer and a fascia layer. The adjustable length cannula 100 includes a body member 112 to which is mounted a cap 116 by means of the engaged threads 114. As with the first embodiment adjustable length cannula 10, the adjustable length cannula 100 includes a slide seal 120 which allows the adjustable length cannula 100 to be sealed against laparoscopic instruments having varying diameters. Further sealing is provided by a main seal 118 which is positioned between the body member 112 and the cap 116. Situated partially within the body member 112 is a cannula member 130, incremental spacing members 132 on the body member 112 and 134 on the cannula member 130, such as complementary raised ribs and indentations or complementary screw threads, allow the longitudinal position of the cannula member 130 with respect to the body member 112 to be adjusted, thereby providing a variable length to the cannula 100. The range of motion of the cannula member 130 is limited by at least one stopper member 136 (see FIG. 13) and a lower raised lip 138. A rubber O-ring seal 140 provides sealing between the cannula member 130 and the body member 112. Cannula member 130 is also provided with a screw thread 142 in order to aid in insertion of the adjustable length cannula 100.

The adjustable length cannula 100 is illustrated in FIG. 8 adjusted to its shortest longitudinal length and inserted through a relatively thin abdominal wall section. It will be appreciated by those skilled in the art that the adjustable length cannula 100 presents a very low profile above the surface of the patient's skin owing to the fact that the body member includes a subcutaneous portion 170, which provides for the adjustability in the length of the cannula 100, lies completely below the surface of the patient's skin. The body member 112 further includes an annular flange portion 172 above the subcutaneous portion 170 which performs the same function as the collet clamp 28 of the first embodiment adjustable length cannula 10 of FIG. 1. As illustrated in FIG. 8, the skin, fat and fascia of the abdominal wall tissue are compressed between the screw threads 142 and the annular flange 172 of the body member 112, thereby providing stability to the adjustable length cannula 100 as well as minimizing tissue trauma in the area of the cannula placement. The low external profile of the adjustable length cannula 100 further reduces accidental movement of the cannula 100, thereby further reducing tissue trauma in the area surrounding the cannula.

Figure 9:
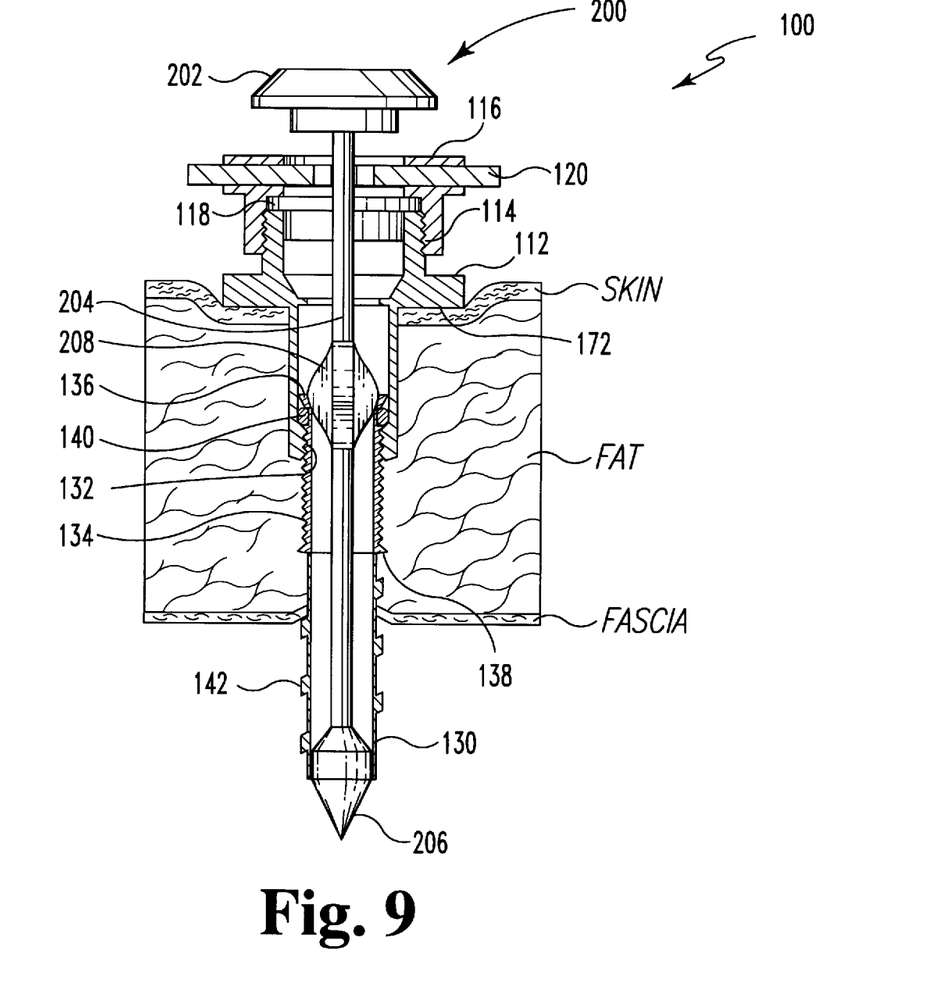
FIG. 9 is a partial cross-sectional side view of the second embodiment adjustable length cannula of the present invention assembled with a second embodiment trocar of the present invention.

Referring now to FIG. 9, the adjustable length cannula 100 is shown in combination with a trocar 200. The trocar 200 includes a disc-shaped handle 202, a longitudinal shaft 204, and a pointed distal end 206. The trocar 200 includes four extensions (or fins) 208 which engage complementary notches 178 in the top of cannula member 130 (see FIG. 13) in order to allow a twisting force to be applied to the cannula member 130. The fins 208 are positioned on the trocar shaft 204 at a position where the pointed distal tip 206 will protrude from the distal end of the cannula member 130 when the fins 208 are engaged with the notches 178 on the top of the cannula member. Engagement of the fins 208 with the cannula member 130 also prevents the trocar 200 from being pushed any further from the distal end of the adjustable length cannula 100.

The adjustable length cannula 100 may be inserted into the patient's body by two different methods. One method of insertion is to insert short. In this method, the cannula member 130 is retracted completely within the body member 112 and the trocar 200 is placed within the adjustable length cannula 100. The trocar 200/cannula 100 is then inserted in the normal fashion until the annular flange 172 of the body member 112 abuts the patient's skin. At this point, the motion is changed to a clockwise rotation of the trocar 200, which in turn creates a clockwise rotation of the cannula member 130. Such rotation causes the cannula member 130 to be extracted from the body member 112 by action of the complementary screw threads 132 and 134. Additionally, as the cannula member 130 is extracted from the body member 112, the screw thread 142 on the cannula member 130 works its way through the abdominal tissue. Such rotation is continued until the tip of the cannula member 130 enters the abdominal cavity. At this point, the adjustable length cannula 100 has been inserted as far as desired by rotation of the trocar 200. By having the wide annular flange 172 of the body member 112 resting on the surface of the skin, there will be no sudden, uncontrolled penetration of the abdominal cavity as with the prior art instruments.

The second method of insertion of the adjustable length cannula 100 is to insert long. In this method, the adjustable length cannula 100 is extended to the desired length and the prior art cannula insertion method is followed until the desired penetration of the abdominal cavity has been achieved. At this point, the body member 112 is rotated while holding the trocar 200 (and consequently the cannula member 130) stationary. Such rotation causes the body member 112 to be screwed down into the patient until the annular flange 172 rests upon the skin, thereby providing a snug fit.

Whether the adjustable length cannula 100 is inserted short or long, when the cannula is in the desired position the trocar is removed. Compression of the patient's skin and fat between the thread 142 and the annular flange surface 172 of the body member 112 establishes a relatively fixed instrument so that there is little lateral instability. This will minimize tissue trauma in the area surrounding insertion and will allow insertion of a surgical instrument through the cannula without the need to steady the cannula with a second hand.

Figures 10, 11:
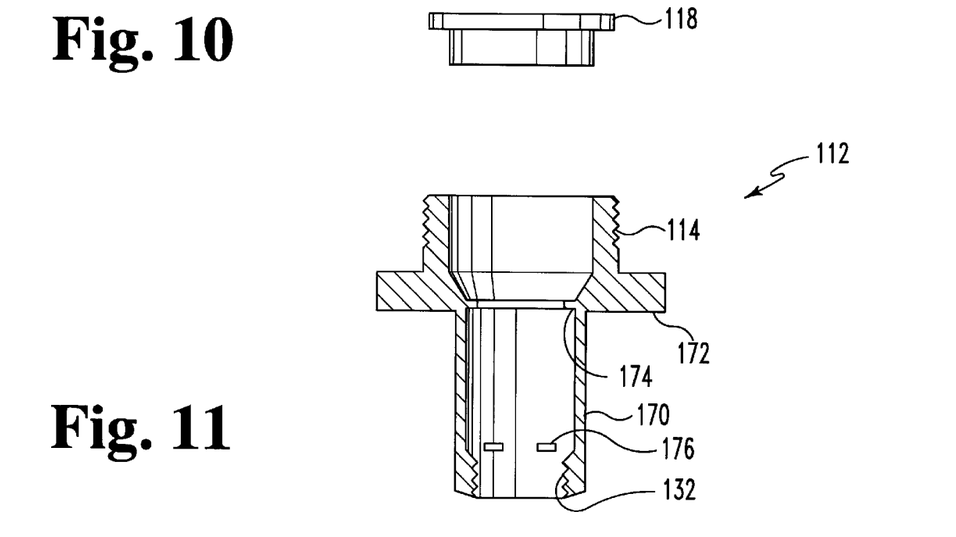
FIG. 10 is a side elevational view of a main valve of the second embodiment adjustable length cannula of the present invention.
FIG. 11 is a cross-sectional side view of a body member of the second embodiment adjustable length cannula of the present invention.

Referring now to FIG. 10, the main seal 118 is shown in a side elevational view. The main seal 118 is preferably formed from silicone or similar materials and includes a slit therethrough in order to allow passage of the trocar 200 and surgical instruments. Referring to FIG. 11, the body member 112 is illustrated in cross-section. A protruding annular ledge 174 is clearly visible in the view of FIG. 11. The ledge 174 interacts with the stopper members 136 of the cannula member 130 in order to prevent the cannula member 130 from moving in the proximal direction beyond the ledge 174 and hitting the main seal 118.

The body member 112 optionally includes a plurality of air ports 176 in order to aid in sterilization of the body member 112.

Figure 12:
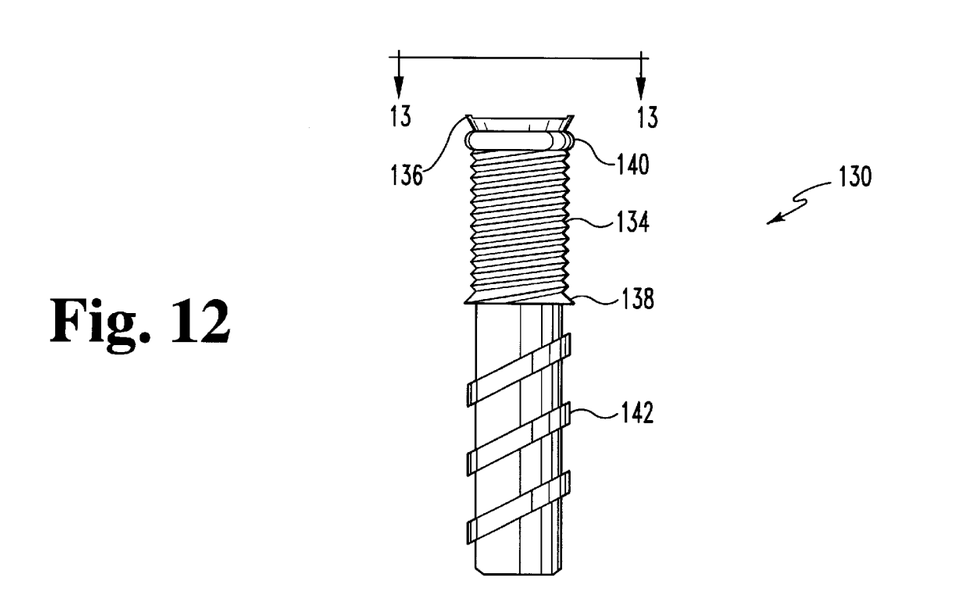
FIG. 12 is a side elevational view of a cannula member of the second embodiment adjustable length cannula of the present invention.

Referring to FIG. 12, the cannula member 130 is illustrated in a side elevational view. The cannula member 130 is inserted into the proximal end of the body member 112. The top stoppers 136 of the cannula member 130 will bend during insertion into the body member 112 and then snap back into position once the cannula member 130 has been inserted into the body member 112. Thereafter, interaction between the top stoppers 136 and the ledge 174 prevent the cannula member 130 from backing out of the top of the body member 112. The cannula member 130 is illustrated in a top plan view in FIG. 13. Notches 178 formed into the top surface of the cannula 130 are clearly visible in this view. The notches 178 engage the fins 208 of the trocar 200 in order to lock the trocar 200 to the cannula 130 for rotation therewith.

Figure 14:
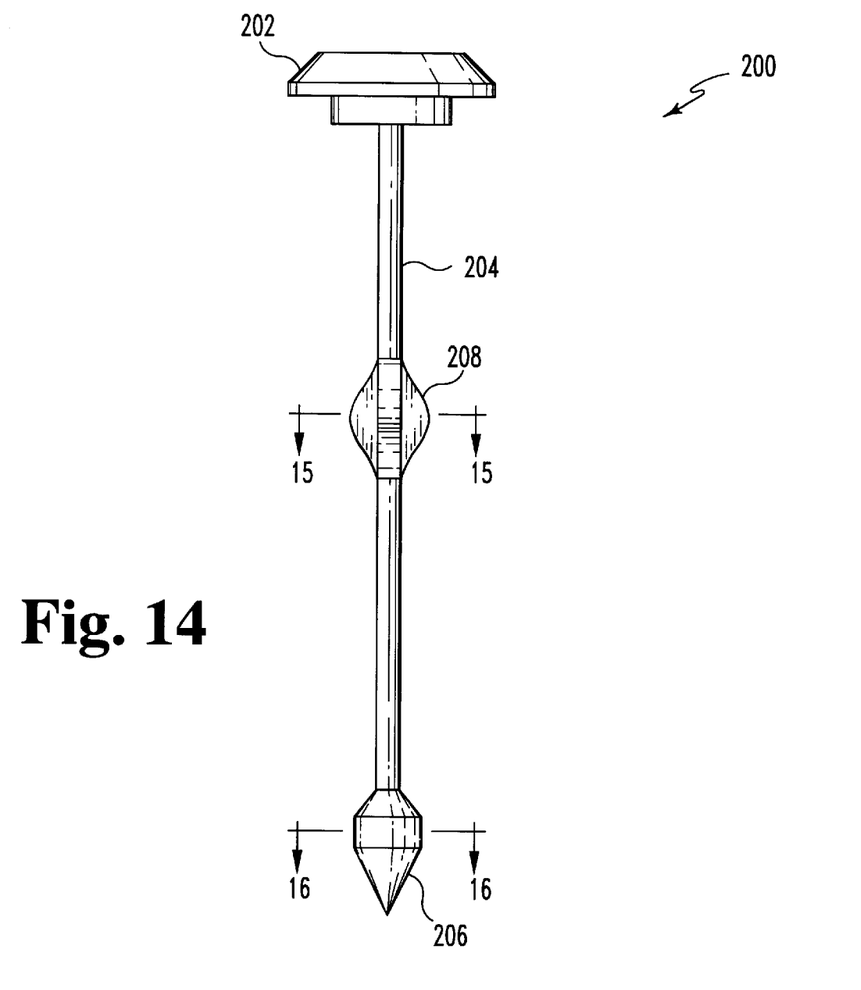
FIG. 14 is a side elevational view of the second embodiment trocar of the present invention.
Figure 15:
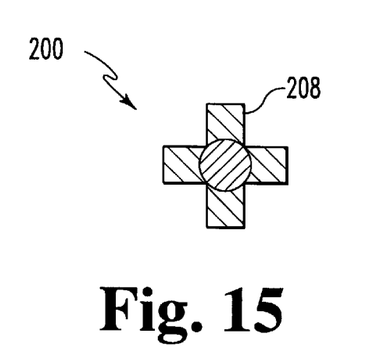
FIG. 15 is a first cross-sectional view of the trocar of FIG. 14.
Figure 16:
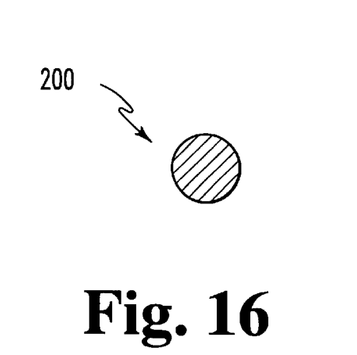
FIG. 16 is a second cross-sectional view of the trocar of FIG. 14.
Figure 17:
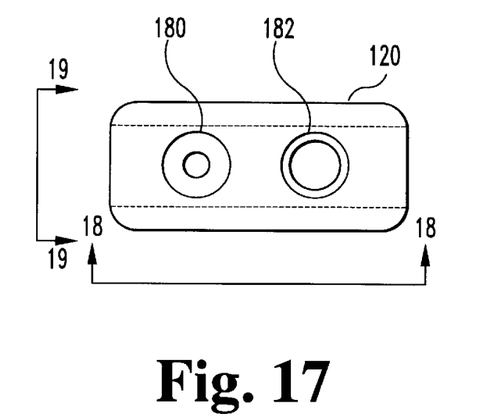
FIG. 17 is a top plan view of a slide seal of the second embodiment adjustable length cannula of the present invention.
Figure 18:
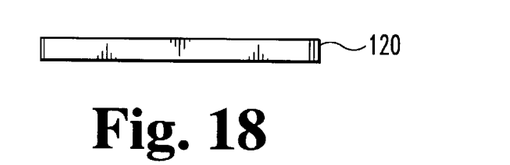
FIG. 18 is a first side elevational view of the slide seal of FIG. 17.
Figure 19:
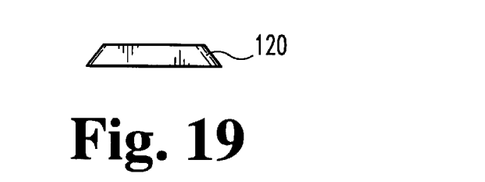
FIG. 19 is a second side elevational view of the slide seal of FIG. 17.
Figure 20:
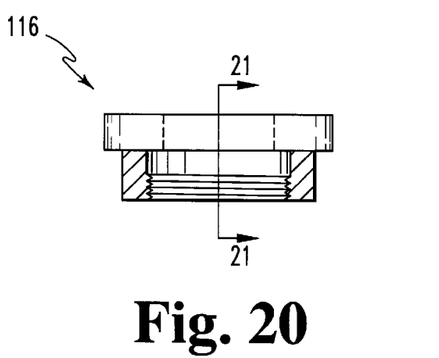
FIG. 20 is a partial cross-sectional side view of a cap of the second embodiment adjustable length cannula of the present invention.
Figure 21:
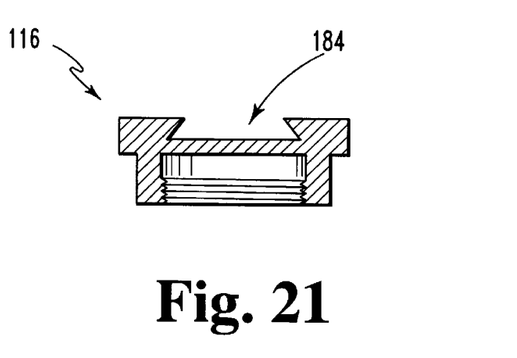
FIG. 21 is a cross-sectional view of the cap of the second embodiment adjustable length cannula of the present invention.

Referring now to FIGS. 14–16, the trocar 200 is illustrated separated from the adjustable length cannula 100. Referring now to FIG. 17, a first embodiment of the slide seal 120 is illustrated in a top plan view. The first embodiment of the slide seal 120 includes a first seal 180 to accommodate relatively narrow instruments and a second seal 182 to accommodate relatively wide instruments. A first side elevational view of the slide seal 120 is illustrated in FIG. 18, while a second side view of the slide seal 120 is illustrated in FIG. 19. The cap 116 is illustrated in a partial cross-sectional side view in FIG. 20, and in a full cross-sectional second side view in FIG. 21. A slot 184 is formed in the cap 116 in order to accommodate the slide seal 120.

The adjustable length cannula 100 preferably measures 0.68 inches from the skin surface to the top of the cannula 100, 2.6 inches from the skin surface to a distal end of the cannula member 130 in a fully extended position, and 2.1 inches from the skin surface to the distal end of the cannula member 130 in a fully retracted position. All of the items disclosed in the present application (except for the seals) may be constructed from plastic, stainless steel, or any other biocompatible material. Additionally, the devices may be disposable or reuseable after sterilization.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. Specifically, the present invention has been illustrated in use with an abdominal wall, however those skilled in the art will appreciate that the present invention may be used to access any body cavity.

What is claimed is:

1. An adjustable length cannula for insertion through a body cavity wall, the adjustable length cannula having a distal end adapted for insertion through a body cavity wall and an oppositely disposed proximal end, the adjustable length cannula, comprising:

a body member, said body member having a surface adapted for abutting a patient's skin;

a cannula member telescopically disposed with respect to the body member;

wherein the body member and the cannula member define an interengaging adjustment structure that allows an overall longitudinal length of the adjustable length cannula to be changed; and wherein at least a portion of said adjustment structure lie distal to said surface.

2. The adjustable length cannula of claim 1, wherein:

said adjustment structure includes first incremental spacing members coupled to the body member and second incremental spacing members coupled to the cannula member, the first and second incremental spacing members being interengaged in order to provide telescoping engagement between the body member and the cannula member; and wherein at least a portion of one of the first and second incremental spacing members lie distal to said surface.

3. The adjustable length cannula of claim 2, wherein the first and second incremental spacing members comprise respective first and second threads.

4. The adjustable length cannula of claim 2, which further includes a flange, and wherein said surface is defined on said flange.

5. The adjustable length cannula of claim 1, wherein more than one half of the telescopically disposed members lie distal to said surface.

6. The adjustable length cannula of claim 1, wherein the body member and the cannula member have at least approximately one-half inch of telescopic adjustment.

7. The adjustable length cannula of claim 1:
wherein said surface on the body member is annular;
wherein the annular surface abuts the skin surface when the adjustable length cannula is inserted through the body cavity wall.

8. The adjustable length cannula of claim 7, further comprising:
a thread at a distal end of the cannula member;
wherein the body cavity wall is compressed between the thread and the annular flange when the adjustable length cannula is inserted through the body cavity wall.

9. The adjustable length cannula of claim 1, further comprising:
an annular ledge on the body member; and
at least one stopper member at a proximal end of the cannula member;
wherein interaction of the annular ledge and the at least one stopper member prevents movement of the cannula member proximal of the annular ledge.

10. The adjustable length cannula of claim 1, further comprising:
at least one notch formed in the cannula member; and
a trocar having at least one extension operable to engage the at least one cannula member notch and to impart a torquing force to the cannula member when the trocar is rotated.

11. The adjustable length cannula of claim 1 wherein said body member and said cannula member are substantially rigid.

12. The adjustable length cannula of claim 1, which further includes:
clamping means for holding said body member to a body wall cavity; and
limiting means for limiting the longitudinal travel of the cannula member relative to said body member.

13. The adjustable length cannula of claim 1 wherein said body member has a constant length, and wherein said constant length defines a distance above the patient's skin when said surface is abutting the patient's skin, and said constant length does not change as the overall longitudinal length of said adjustable length cannula is changed.

14. An adjustable length cannula for insertion through a body cavity wall, comprising:
a body member;
a cannula member telescopically disposed with respect to the body member;
a clamp member adjustably engaged with the body member and including an annular flange;

wherein the annular flange abuts a skin surface when the adjustable length cannula is inserted through the body cavity wall;
wherein the telescopic disposition of the body member and the cannula member allows an overall longitudinal length of the adjustable length cannula to be changed;
an adjustable length trocar extending through the body member and the cannula member;
wherein the adjustable length trocar further comprises:
a longitudinal shaft;
a handle at a proximal end of the shaft;
a pointed tip at a distal end of the shaft;
an upper trocar housing rotatably coupled to the longitudinal shaft and having third incremental spacing members thereon; and
a lower trocar housing engaged with a proximal end of the body member and having fourth incremental spacing members thereon, the third and fourth incremental spacing members being interengaged in order to allow the shaft to telescope within the body member and the cannula member.

15. An adjustable length cannula for insertion through a body cavity wall, comprising:
a body member;
a cannula member telescopically disposed with respect to the body member;
a clamp member adjustably engaged with the body member and including an annular flange;
wherein the annular flange abuts a skin surface when the adjustable length cannula is inserted through the body cavity wall;
wherein the telescopic disposition of the body member and the cannula member allows an overall longitudinal length of the adjustable length cannula to be changed;
an adjustable length trocar extending through the body member and the cannula member;
wherein the adjustable length trocar further comprises:
a longitudinal shaft;
a handle at a proximal end of the shaft;
a pointed tip at a distal end of the shaft, wherein the pointed tip has a threaded surface;
an upper trocar housing rotatably coupled to the longitudinal shaft and having third incremental spacing members thereon; and
a lower trocar housing engaged with a proximal end of the body member and having fourth incremental spacing members thereon, the third and fourth incremental spacing members being interengaged in order to allow the shaft to telescope within the body member and the cannula member.

16. An adjustable length cannula for insertion through a body cavity wall, comprising:
a body member;
a cannula member telescopically disposed with respect to the body member;
wherein the telescopic disposition of the body member and the cannula member allows an overall longitudinal length of the adjustable length cannula to be changed;
wherein at least a portion of the telescopically disposed portions of the cannula member and the body member lie below a skin surface when the adjustable length cannula is inserted through the body cavity wall;
at least one notch formed in the cannula member; and
a trocar having at least one extension operable to engage the at least one cannula member notch and to impart a torquing force to the cannula member when the trocar is rotated, wherein the trocar includes a threaded distal end.

17. An adjustable length cannula for insertion through a body cavity wall, said adjustable length cannula having a distal end adapted for insertion through a body cavity wall and an oppositely disposed proximal end, said adjustable length cannula comprising:

a body member;

a cannula member telescopically disposed with respect to the body member;

a clamp member adjustably engaged with the body member and including a flange;

wherein the flange abuts a skin surface when the distal end of the adjustable length cannula is inserted through a body cavity wall;

wherein the body member and the cannula member interengage to form a longitudinal adjuster that allows an overall longitudinal length of the adjustable length cannula to be changed; and wherein at least a portion of the longitudinal adjuster lie distal to the flange.

18. The adjustable length cannula of claim 17, when:

said longitudinal adjuster includes a plurality of first incremental spacing members coupled to the body member and a plurality of second incremental spacing members coupled to the cannula member, the first and second incremental spacing members being interengaged in order to provide telescoping engagement between the body member and the cannula member; and wherein at least a portion of the first and second incremental spacing members lie distal to the flange.

19. The adjustable length cannula of claim 18, wherein the first and second incremental spacing members comprise respective first and second threads.

20. The adjustable length cannula of claim 18, further comprising:

a raised lip on the cannula member distal of the second incremental spacing member;

wherein interaction of the raised lip and a distal end of the body member prevents movement of the raised lip proximal of the distal end of the body member.

21. The adjustable length cannula of claim 17, wherein more than one half of the telescopically disposed members lie distal to the flange.

22. The adjustable length cannula of claim 17, wherein the body member and the cannula member have at least approximately one-half inch of telescopic adjustment.

23. The adjustable length cannula of claim 17, further comprising:

a thread at a distal end of the cannula member;

wherein the body cavity wall is compressed between the thread and the annular flange when the adjustable length cannula is inserted through the body cavity wall.

24. The adjustable length cannula of claim 17, further comprising:

an adjustable length trocar extending through the body member and the cannula member.

* * * * *

UNITED STATES PATENT AND TRADEMARK OFFICE
CERTIFICATE OF CORRECTION

PATENT NO : 5,882,344

DATED : March 16, 1999

INVENTOR(S) : Albert E. Stouder, Jr.

It is certified that error appears in the above-identified patent and that said Letters Patent are hereby corrected as shown below:

On the cover page, under the prior art References Cited, U.S. Patent No. 2,198,666 change the date of the patent from "4/1879" to --4/1940--.

On the cover page, in the Abstract, please delete the current Abstract and insert therefor
--An adjustable length cannula and trocar used in the performance of laparoscopic or arthroscopic surgery. The adjustable length cannula can be longitudinally extended or retracted in order to accommodate the differences in body cavity wall thickness. The adjustable length cannula includes a body member adapted for abutting the patient's skin and a cannula member that interengage so as to define an adjustable structure that allows the overall longitudinal length of the cannula to be changed. At least a portion of the interengaging adjustable structure lies beneath the patient's skin as to maintain a low profile for the cannula.--

Signed and Sealed this

Twelfth Day of September, 2000

*Attest:*

Q. TODD DICKINSON

*Attesting Officer*  *Director of Patents and Trademarks*